(12) United States Patent
Stoyanov et al.

(10) Patent No.: US 12,343,417 B2
(45) Date of Patent: Jul. 1, 2025

(54) ANTIPERSPIRANT COMPOSITIONS

(71) Applicant: Conopco, Inc., Trumbull, CT (US)

(72) Inventors: Simeon Dobrev Stoyanov, Spijkenisse (NL); Philip Christopher Waterfield, Heswall (GB); Aneliya Nikolova Zdravkova, Liverpool (GB)

(73) Assignee: Conopco, Inc., Hoboken, NJ (US)

( * ) Notice: Subject to any disclaimer, the term of this patent is extended or adjusted under 35 U.S.C. 154(b) by 723 days.

(21) Appl. No.: 17/283,748

(22) PCT Filed: Nov. 4, 2019

(86) PCT No.: PCT/EP2019/080099
§ 371 (c)(1),
(2) Date: Apr. 8, 2021

(87) PCT Pub. No.: WO2020/094568
PCT Pub. Date: May 14, 2020

(65) Prior Publication Data
US 2021/0378927 A1    Dec. 9, 2021

(30) Foreign Application Priority Data
Nov. 6, 2018   (EP) .................................. 18204724

(51) Int. Cl.
| | | |
|---|---|---|
| A61K 8/36 | (2006.01) | |
| A61K 8/06 | (2006.01) | |
| A61K 8/19 | (2006.01) | |
| A61K 8/27 | (2006.01) | |
| A61K 8/73 | (2006.01) | |
| A61Q 15/00 | (2006.01) | |

(52) U.S. Cl.
CPC .............. *A61K 8/361* (2013.01); *A61K 8/062* (2013.01); *A61K 8/19* (2013.01); *A61K 8/27* (2013.01); *A61K 8/731* (2013.01); *A61K 8/737* (2013.01); *A61Q 15/00* (2013.01); *A61K 2800/48* (2013.01); *A61K 2800/5422* (2013.01); *A61K 2800/5426* (2013.01); *A61K 2800/874* (2013.01)

(58) Field of Classification Search
CPC .......... A61K 8/361; A61K 8/062; A61K 8/19; A61K 8/27; A61K 8/731; A61K 8/737; A61K 2800/48; A61K 2800/5422; A61K 2800/5426; A61K 2800/874; A61Q 15/00
See application file for complete search history.

(56) References Cited

U.S. PATENT DOCUMENTS

| | | | |
|---|---|---|---|
| 4,172,123 A | 10/1979 | Lowicki | |
| 4,968,496 A | 11/1990 | Rohe et al. | |
| 5,409,694 A | 4/1995 | Meyer et al. | |
| 5,593,663 A | 1/1997 | Leng et al. | |
| 6,605,288 B1 | 8/2003 | Okawa et al. | |
| 7,501,136 B2 | 3/2009 | Hagura et al. | |
| 2009/0092568 A1 | 4/2009 | Mabrouk | |
| 2014/0173833 A1* | 6/2014 | Banowski | A61K 8/466 424/68 |
| 2015/0086499 A1* | 3/2015 | Doering | A61K 8/731 424/68 |
| 2016/0235637 A1 | 8/2016 | Britze | |
| 2019/0274935 A1 | 9/2019 | Pambou et al. | |
| 2019/0298625 A1 | 10/2019 | Hilliard, Jr. et al. | |

FOREIGN PATENT DOCUMENTS

| | | | |
|---|---|---|---|
| CA | 1097223 | 3/1981 | |
| CN | 108060004 | 5/2018 | |
| CN | 110124042 | 8/2019 | |
| DE | 2503963 | 8/1976 | |
| EA | 202190338 | 9/2021 | |
| EP | 0545556 | 6/1993 | |
| EP | 0550960 | 7/1993 | |
| EP | 1973514 | 4/2009 | |
| JP | 2005206573 A  * | 8/2005 | .............. A61K 7/00 |
| WO | WO0152805 | 7/2001 | |
| WO | WO2010145905 | 12/2010 | |
| WO | WO2011029516 | 3/2011 | |
| WO | WO-2013149323 A1 * | 10/2013 | .............. A61K 8/42 |
| WO | WO2015051805 | 4/2015 | |
| WO | WO2018111664 | 6/2018 | |
| WO | WO2019206466 | 10/2019 | |
| WO | WO2020078931 | 4/2020 | |
| WO | WO2020094568 | 5/2020 | |

OTHER PUBLICATIONS

Lambers et al. Natural skin surface pH is on average below 5, which is beneficial for its resident flora. Int J Cosmet Sci 2006, 28(5): 359-370. (Year: 2006).*
Search Report and Written Opinion in PCTEP2021084279; Mar. 11, 2022; World Intellectual Property Org. (WIPO).
Written Opinion 2 in PCTEP2021084279; Nov. 17, 2022; World Intellectual Property Org. (WIPO).
GNPD Database (Online) Mintel; Foaming Deodorant Lotion (Mint); Kao Men's Biore; Apr. 2008; pp. 1-2, XP055893288, Record ID 893181; Japan.
Marianne Brandt et al.; Influence of climatic conditions on antiperspirant efficacy determined at different test areas; Skin Research and Technology; 2008; pp. 213-219; vol. 14; The Authors; Singapore.
Search Report and Written Opinion in EP 20212213; Jun. 4, 2021; European Patent Office (EPO).
GNPD Mintel; 24H Balm Deo Roll On; Muller Aveo Med; Mar. 2019; pp. 1-2, XP055581254, Record ID 6396927; Germany.
(Continued)

*Primary Examiner* — Robert A Wax
*Assistant Examiner* — Olga V. Tcherkasskaya
(74) *Attorney, Agent, or Firm* — Stephanie Huang

(57) ABSTRACT

An oil-in-water emulsion comprising a liquid $C_{10}$-$C_{22}$ fatty acid, an emulsifier and a water-soluble metal salt capable of forming a water-insoluble salt with the $C_{10}$-$C_{22}$ fatty acid at a pH of greater than 6 and thereby giving an antiperspirancy benefit on topical application to the skin.

18 Claims, 2 Drawing Sheets

(56) References Cited

OTHER PUBLICATIONS

Search Report in EP18204724; May 17, 2019; European Patent Office (EPO).
GNPD Mintel; 48h Antiperspirant Roll-On; Ducray Hidrosis Control; Jun. 2018; pp. 1-4, Record ID 5757709, XP055581258; France.
Search Report and Written Opinion in PCTEP2019080099; Feb. 12, 2020; World Intellectual Property Org. (WIPO).

* cited by examiner

ANTIPERSPIRANT COMPOSITIONS

CROSS REFERENCE TO RELATED APPLICATIONS

The present application is a U.S. National Phase Application under 35 U.S.C. § 371 of International Application No. PCT/EP2019/080099, filed on Nov. 4, 2019, which claims priority to European Patent Application No. 18204724.1, filed on Nov. 6, 2018, the contents of which are incorporated herein in their entireties.

FIELD OF INVENTION

The present invention concerns antiperspirant compositions and methods of reducing perspiration. It is particular concerned with such compositions and methods that do not involve the use of aluminium salts.

BACKGROUND

Traditionally, antiperspirant compositions use astringent aluminium or aluminium-zirconium salts to deliver their antiperspirant benefit. These antiperspirant salts function by blocking the top part of sweat glands and thereby reducing the release of sweat from these glands.

Many parties have investigated alternative, non-aluminium antiperspirant actives and compositions. Some of these have involved reducing the production of sweat by the secretory coil of the sweat glands; however, actives functioning in this manner may be considered therapeutic in nature, which may be undesirably for formulations intended for use as cosmetic products.

Alternative non-aluminium antiperspirant actives and compositions that function by blocking the sweat glands have also been devised.

WO 2010/145905 (Unilever, 2010) discloses the use lamellar phase stabilised oil-in-water emulsions as antiperspirant agents.

EP 550,960 A1 (Unilever, 1992) discloses the use as an antiperspirant active of an amphiphilic material which forms, upon contact with perspiration, a water-insoluble liquid crystal phase of greater than one dimensional periodicity.

WO 2018/111664 (Colgate, 2018) discloses antiperspirant compositions comprising a zinc-based antiperspirant active, a thickener comprising a $C_{14}$-$C_{22}$ fatty acid salt and a carrier comprising a polyhydric alcohol, optionally with water.

There are also multiple disclosures of antiperspirant salts comprising sodium stearate as a structurant; however, stearic acid is not a fatty acid as used in the present invention and the sodium soap is not formed in situ in such usage, in the manner that the soap is created in the present invention.

There are a limited number of disclosures of calcium salts of organic acids being used in antiperspirant compositions. WO 2015/051805 A1 (Riemann Trading Aps, 2015) discloses anhydrous antiperspirant compositions comprising aluminium chloride or any hydrates thereof; at least one calcium or magnesium salt of an organic acid and a water-miscible solvent. However, there is no disclosure of the mixture of carboxylic acids and water-soluble salts in accordance with the invention herein described.

CA1097223 (American Cyanamid Company, 1981) discloses an antiperspirant stick comprising 20-50% ethanol, 15-25% aluminum chlorohydrate, 15-60% of a C16 fatty alcohol and 0-10% of a magnesium or calcium salt of a long chain fatty acid.

SUMMARY OF INVENTION

Figure 1:
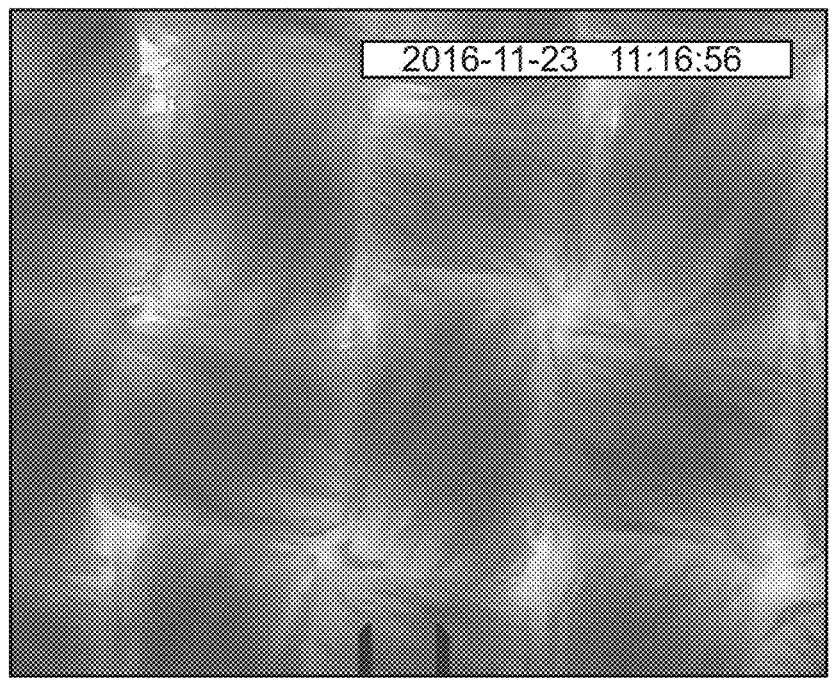
FIG. 1 is a microscopy image of treated fabric.

It is an objective of the present invention to reduce perspiration from the surface of the human body, particularly in the underarm regions, otherwise known as the axillae.

It is a further objective of the present invention to reduce perspiration from the surface of the human body by blockage or partial blockage of sweat glands without the use of astringent aluminium or zirconium salts.

In a first aspect of the invention, there is provided an oil-in-water emulsion comprising (i) a $C_{10}$-$C_{22}$ fatty acid which is liquid; (ii) an emulsifier for the $C_{10}$-$C_{22}$ fatty acid and (iii) a water-soluble metal salt capable of forming a water-insoluble salt with the $C_{10}$-$C_{22}$ fatty acid at a pH of greater than 6.

In preferred embodiments, the water-insoluble salt is capable of forming a solid, water-insoluble salt with the $C_{10}$-$C_{22}$ fatty acid at a pH of greater than 6, particularly at a temperature of 37° C.

In a second aspect of the invention, there is provided a method of reducing perspiration comprising the topical application of an emulsion according to the first aspect of the invention.

In a third aspect of the invention, there is provided a method of manufacture of an antiperspirant composition comprising the steps of emulsifying a $C_{10}$-$C_{22}$ fatty acid which is liquid in an aqueous continuous phase, adding a water-soluble metal salt to the aqueous continuous phase, the water-soluble metal salt being capable of forming a water-insoluble salt with the $C_{10}$-$C_{22}$ fatty acid at a pH of greater than 6.

In the third aspect of the invention, the addition of the water-soluble metal salt to the aqueous phase may be before or after the emulsification of the $C_{10}$-$C_{22}$ fatty acid.

In the third aspect of the invention, the emulsification of the $C_{10}$-$C_{22}$ fatty acid is performed using an emulsifier.

In a fourth aspect of the invention, there is provided a method of reducing perspiration comprising the pH-triggered in situ generation of a water-insoluble salt of a $C_{10}$-$C_{22}$ fatty acid, the water-insoluble salt being generated from a topically-applied $C_{10}$-$C_{22}$ fatty acid which is liquid and a water-soluble metal salt.

In the fourth aspect of the invention, the $010$-$C_{22}$ fatty acid is typically applied from an oil-in-water emulsion stabilised by an emulsifier. The water-soluble metal salt is preferably dissolved in the water phase of the oil-in-water emulsion.

The method of reducing perspiration is generally on the skin of the human body, in particular the axillae.

The "in situ" generation of the antiperspirant active, i.e. the water-insoluble salt of the $C_{10}$-$C_{22}$ fatty acid, refers to the formation of this material on the skin of the human body; in particular, in the sweat ducts present in the skin of the human body, especially in the axillae.

The "pH-triggered" aspect of the antiperspirant active generation is caused by the pH of the sweat on the skin being somewhat higher than the pH of the oil-in-water emulsion of the $C_{10}$-$C_{22}$ fatty acid. In preferred embodiments, the oilin-water emulsion of the $C_{10}$-$C_{22}$ fatty acid is at its natural pH or is slightly acidified, to pH 3.5 to 4.5, for example. On application to the skin (sweat pH ca. 6 to 7) the water-soluble metal salt forms a gel with the fatty acid and causes blockage of sweat ducts.

In a fifth aspect of the invention, there is provided the use of an in situ generated water-insoluble salt of a liquid $C_{10}$-$C_{22}$ fatty acid as an antiperspirant agent.

DETAILED DESCRIPTION

Herein, all amounts, parts, percentages and ratios are by weight and relate to the total composition, unless otherwise indicated. This also applies to the examples.

Herein, the term comprising is used non-exhaustively.

Herein, preferences expressed with regard to one aspect of the invention apply, to the extent possible, with regard to any other aspect of the invention.

Herein, preferences expressed with regard to one feature are preferably used in combination with preferences expressed for one or more other features.

Herein, when a component is referred to in the singular, it is to be understood that multiple components of the type referred to could be present and all should be included in calculating any amount or ratio specified.

Herein, states of matter such as solid, liquid and gas relate to the specified state of matter at 25° C. and atmospheric pressure. For example, the "liquid" $C_{10}$-$C_{22}$ fatty acid used in the present invention is liquid at 25° C. and one atmosphere pressure.

Herein, quoted viscosities are measured at 37° C. and at a shear rate of 0.01 $s^{-1}$.

Herein, the terms gel and gelation refer to states of matter and formations of states of matter that might comprise crystalline solids, amorphous solids, or viscous states of matter capable of blocking sweat glands. The gel referred to is typically of viscosity of at least 2 Pa·s, preferably at least 5 Pa·s, more preferably at least 10 Pa·s, and most preferably at least 100 Pa·s. The "gel" may be a solid, crystalline or amorphous, or may have a viscosity of up to 1000 Pa·s.

Herein, references to "compositions" [of the invention] equate to "emulsions" [of the invention].

Fatty Acid

The $C_{10}$-$C_{22}$ fatty acid used in accordance with the invention must be a liquid. Such fatty acids are typically unsaturated, meaning that they have one or more unsaturated carbon-carbon bonds.

Preferably, the $C_{10}$-$C_{22}$ fatty acid used in accordance is liquid at 20° C. and more preferably it is liquid at 10° C. Having a relatively low melting point for the fatty acid can enhance the low temperature storage stability for compositions of the invention.

The $C_{10}$-$C_{22}$ fatty acid preferably has from 14 to 20 carbon atoms, more preferably from 16 to 18 carbon atoms and most preferably 18 carbon atoms. Preferred $C_{18}$ fatty acids are unsaturated, having at least one double bond. Particularly preferred fatty acids are oleic, linoleic, linolenic and ricinoleic acid. Especially preferred are oleic and ricinoleic acid.

Mixtures of $C_{10}$-$C_{22}$ fatty acids may be used in some embodiments.

The total amount of C10-C22 fatty acid in compositions of the invention is preferably from 3% by weight of the composition, more preferably from 4.5% by weight of the composition, and most preferably from 6% by weight of the composition. Independently and in conjunction with each of the preferred lower levels indicated above, the total amount of C10-C22 fatty acid is preferably up to 15% by weight of the composition, more preferably up to 12.5% by weight of the composition, and most preferably up to 10% by weight of the composition.

In certain preferred embodiments, the total amount of C10-C22 fatty acid is from 5 to 10% by weight of the composition.

Water-Soluble Metal Salt

The water-soluble metal salt has a solubility in water of at least 10 g/L and preferably at least 100 g/L, solubilities being measured at 25° C.

The water-soluble metal salt is typically polyvalent, preferably divalent and more preferably selected from calcium and zinc salts. Zinc salts are particularly preferred, especially when the fatty acid is ricinoleic acid.

Mixtures of water-soluble metal salts may be used in some embodiments.

The total amount of water-soluble metal salts in compositions of the invention is preferably from 0.75% by weight of the composition, more preferably from 1.0% by weight of the composition, and most preferably from 1.3% by weight of the composition. Independently and in conjunction with each of the preferred lower levels indicated above, the total amount of water-soluble metal salt is preferably up to 3.0% by weight of the composition, more preferably up to 2.5% by weight of the composition, and most preferably up to 2% by weight of the composition.

In certain preferred embodiments, the total amount of water-soluble metal salts is from 1.5 to 2.0% by weight of the composition.

The molar ratio of the $C_{10}$-$C_{22}$ fatty acid to the cation of the water-soluble metal salt (divided by its valence), is preferably selected to be from 1:2 to 2:1, more preferably from 2:3 to 3:2 and most preferably about 1:1. In this way, neither too much of the $C_{10}$-$C_{22}$ fatty acid nor too much of the water-soluble metal salt is wasted. To clarify, these ratios may be expressed as preferably from 33:67 to 67:33; more preferably from 40:60 to 60:40 and most preferably about 503:50.

When the water-soluble metal salt is divalent, such as a calcium salt or zinc salt, particularly calcium chloride or zinc chloride, the molar ratio of the water-soluble metal salt to the $C_{10}$-$C_{22}$ fatty acid is preferably selected to be from. 1:4 to 1:1, more preferably from 1:3 to 2:3 and most preferably about 1:2. To clarify, these ratios may be expressed as preferably from 20:80 to 50:50; more preferably from 25:75 to 40:60 and most preferably about 33:67.

Water-Insoluble Salt Formed with the $C_{10}$-$C_{22}$ Fatty Acid at a pH of Greater than 6

The Ability of the Water-Soluble Metal Salt to Form a Water-Insoluble Salt with the $C_{10}$-$C_{22}$ Fatty acid at a pH of greater than 6 is a key feature of the present invention. This may be tested by bringing together the components at a pH of greater than 6 and a temperature of 20° C., 25° C. or 37° C. In a preferred method of testing, the components are co-formulated at a pH of 3.5 and the pH of the mixture is then adjusted to greater than 6 using a base.

Herein, "water-insoluble" means having a solubility in water of less than 10 g/L at 25° C., preferably less than 1 g/L.

Emulsifier

The emulsifier is an essential component of the compositions of the invention. Any emulsifier capable of emulsifying the $C_{10}$-$C_{22}$ fatty acid in water at a temperature of 20° C. may be used. Mixtures of emulsifiers may also be used.

Preferably, the emulsifier or mixture of emulsifiers comprises a nonionic emulsifier. In certain preferred embodiments, a mixture of emulsifiers is used, such as a mixture of nonionic emulsifiers or a mixture of a nonionic emulsifier and an anionic emulsifier.

The total amount of emulsifier in compositions of the invention is preferably from 0.5% by weight of the composition, more preferably from 1.0% by weight of the composition, and most preferably from 1.3% by weight of the composition. Independently and in conjunction with each of the preferred lower levels indicated above, the total amount of emulsifier is preferably up to 10% by weight of the composition, more preferably up to 7.5% by weight of the composition, and most preferably up to 5% by weight of the composition.

The weight ratio of the emulsifier to the C10-C22 fatty acid is preferably from 1:10, more preferably from 1:8 and most preferably from 1:6. Independently and in conjunction with each of the preferred ratios indicated above, the weight ratio of the emulsifier to the C10-C22 fatty acid is preferably up to 2:3, more preferably up to 1:2 and most preferably up to 1:3.

In certain preferred embodiments, the emulsifier comprises a polyglyceryl ester, such as polyglyceryl-3 stearate. When the emulsifier comprises such materials, the weight ratio of the emulsifier to the C10-C22 fatty acid is preferably from 1:10, more preferably from 1:7 and most preferably from 1:4. Independently and in conjunction with each of the preferred weight ratios indicated above, the weight ratio of the emulsifier to the C10-C22 fatty acid is preferably up to 1:1, more preferably up to 9:11 and most preferably up to 2:3. In an especially preferred embodiment, the weight ratio of the polyglyceryl ester containing emulsifier to the C10-C22 fatty acid is from 1:4 to 2:3, i.e., from 20:80 to 40:60.

In certain preferred embodiments, the emulsifier comprises a linear alkyl ethoxylate, such as Steareth-20. Preferred linear alkyl ethoxylates have at least 10 ethoxylate units per molecule and particularly preferred linear alkyl ethoxylates have at least 15 ethoxylate units per molecule.

When the emulsifier consists of only linear alkyl ethoxylate, the weight ratio of the emulsifier to the C10-C22 fatty acid is preferably from 5:95 to 30:70, more preferably from 10:90 to 28:72 and most preferably from 15:85 to 25:75.

The preferred emulsifiers and preferred ratios of emulsifier to the $C_{10}$-$C_{22}$ fatty acid are important for the stability of the composition, by which is meant its phase stability, i.e. its lack of phase separation over an extended period.

Additional Features

A highly preferred additional feature is a thickener. A thickener serves to increase the viscosity of compositions of the invention and can enhance the consumer appeal thereof. The thickener can also aid the phase stability of the composition and/or the ability of the composition to be retained within a roll-on dispenser without leakage.

Thickeners suitable for use with the present invention include cationic and nonionic polymers, particularly naturally derived cationic and nonionic polymeric thickeners, examples including guar gum and derivatives and cellulose derivatives, such as hydroxyethylcellulose. Especially preferred thickeners are cationic polymers, in particular guar gum and/or derivatives thereof.

A thickener is typically employed at from 0.1 to 10% by weight of the total composition. In preferred embodiments, the thickener is present at from 0.2 to 5% by weight of the total composition, and in more preferred embodiments, it is present at from 0.3 to 3% by weight of the total composition.

In a preferred embodiment, the composition of the invention is stored in a roll-on dispenser and is dispensed therefrom. Compositions of the invention are particularly suited to being stored and dispensed from a roll-on dispenser designed to be kept in an inverted position for extended periods. For the avoidance of doubt, "an inverted position" for a roll-on dispenser is with the roll-on applicator, usually a ball, located below the reservoir containing the composition.

A thickener is a preferred component of compositions to be stored and dispensed from a roll-on dispenser.

In another preferred embodiment, the composition of the invention is stored in a pump spray or squeeze spray dispenser and is dispensed therefrom.

In another preferred embodiment, the composition has the form of a cream, typically having a viscosity of from 10 to 100 Pa·s. Such compositions can have particularly good storage stability.

A thickener is a highly preferred component of compositions to be stored and dispensed from a roll-on dispenser.

In another embodiment, the composition has the form of a soft solid, typically having a viscosity of from 100 to 1000 Pa·s. A thickener is an essential component of such compositions. Such compositions can have particularly good storage stability.

In another embodiment, the composition has the form of a solid stick. A thickener is an essential component of such compositions.

A preservative is a preferred additional component in compositions of the invention. A preservative serves to reduce or eliminate microbial contamination of compositions of the invention. Preservatives are typically employed at a total level of from 0.05 to 3%, preferably at from 0.1 to 2% by weight of the composition, and most preferably at from 0.4 to 1% by weight of the composition.

Suitable preservatives for use with the present invention include 2-phenoxyethanol, iodopropynyl butylcarbamate, $C_1$-$C_3$ alkyl parabens, sodium benzoate, caprylyl glycol and ethylenediaminetetraacetic acid (EDTA). Particularly preferred preservatives are 2-phenoxyethanol, iodopropynyl butylcarbamate, sodium benzoate, caprylyl glycol and EDTA and especially preferred are 2-phenoxyethanol and iodopropynyl butylcarbamate.

An antimicrobial deodorant active is a preferred an additional component in compositions of the invention. Such components serve to reduce or eliminate body odour by reducing or otherwise impeding the function of microbes on the skin of the body responsible for malodour generation.

The antimicrobial deodorant active may also be a preservative for the composition.

When employed, the anti-microbial deodorant agent is typically incorporated into the composition at from 0.01% to 3% by weight of the composition, and particularly at from 0.03% to 0.5% by weight of the composition.

Preferred anti-microbial deodorant agents have a minimum inhibitory concentration (MIC) of 1 mg·ml$^{-1}$ or less, particularly 200 mg·ml$^{-1}$ or less, and especially 100 μg·ml$^{-1}$ or less. The MIC of an anti-microbial agent is the minimum concentration of the agent required to significantly inhibit microbial growth. Inhibition is considered "significant" if an 80% or greater reduction in the growth of an inoculum of *Staphylococcus epidermidis* is observed, relative to a control medium without an anti-microbial agent, over a period of 16 to 24 hours at 37° C. Details of suitable methods for determining MICs can be found in "Antimicrobial Agents and Susceptibility Testing", C. Thornsberry, (in "Manual of Clinical Microbiology", 5$^{th}$ Edition, Ed. A. Balows et al, American Society for Microbiology, Washington D.C., 1991). A particularly suitable method is the Macrobroth Dilution Method as described in Chapter 110 of above publication (pp. 1101-1111) by D. F. Sahm and J. A. Washington II. MICs of anti-microbials suitable for inclusion in the compositions of the invention are triclosan: 0.01-10 μg·ml$^{-1}$ (J. Regos et al., Dermatologica (1979), 158: 72-79) and farnesol: ca. 25 μg·ml$^{-1}$ (K. Sawano, T. Sato, and R. Hattori, Proceedings of the 17$^{th}$ IFSCC International Conference, Yokahama (1992) p. 210-232). By contrast ethanol and similar alkanols have MICs of greater than 1 mg·ml$^{-1}$.

Suitable organic anti-microbials are bactericides, for example quaternary ammonium compounds, like cetyltrimethylammonium salts; chlorhexidine and salts thereof; and diglycerol monocaprate, diglycerol monolaurate, glycerol monolaurate, and similar materials, as described in "Deodorant Ingredients", S. A. Makin and M. R. Lowry, in "Antiperspirants and Deodorants", Ed. K. Laden (1999, Marcel Dekker, New York). More preferred antimicrobials for use in the compositions of the invention are polyhexamethylene biguanide salts (also known as polyaminopropyl biguanide salts), an example being Cosmocil CQ™, which is made commercially available by Zeneca PLC, preferably used at up to 1% by weight of the composition, and more preferably at 0.03% to 0.3% by weight of the composition; 2',4,4'-trichloro,2-hydroxy-diphenyl ether (triclosan), preferably used at up to 1% by weight of the composition, and more preferably at 0.05-0.3% by weight of the composition; and 3,7,11-trimethyldodeca-2,6, 10-trienol (farnesol), preferably used at up to 1% by weight of the composition and more preferably at up to 0.5% by weight of the composition.

Other suitable organic antimicrobial agents are transition metal chelators, as described in WO01/52805, for example. Transitional metal chelators having a binding coefficient for iron(III) of greater than 10$^{26}$, for example diethylenetriaminepentaacetic acid and salts thereof are preferred.

Antioxidants may be advantageously employed in certain compositions, in particularly those comprising unsaturated fatty acid. Antioxidants that may be used include butylated hydroxytoluene (BHT), butylated hydroxyanisole (BHA) and pentaerythrityl tetra-di-t-butyl hydroxyhydrocinnamate. Antioxidants may be used at from 0.05 to 5% by weight of the composition, in particular at from 0.075 to 2.5% by weight of the composition, and especially at from 0.1 to 1% by weight of the composition.

Certain sensory modifiers are further desirable components. Such materials are preferably used at a level of up to 20% by weight of the composition. Emollients, humectants, volatile oils, non-volatile oils, and particulate solids which impart lubricity are all suitable classes of sensory modifiers. Examples of such materials include cyclomethicone, dimethicone, dimethiconol, isopropyl myristate, isopropyl palmitate, talc, finely-divided silica (e.g., sold under the tradename Aerosil 200), particulate polyethylene (e.g., sold under the tradename Acumist B18), polysaccharides, corn starch, C12-C15 alcohol benzoate, polypropylene glycol-3 (PPG-3) myristyl ether, octyl dodecanol, C7-C14 isoparaffins, di-isopropyl adipate, isosorbide laurate, polypropylene glycol-14 (PPG-14)butyl ether, glycerol, hydrogenated polyisobutene, polydecene, titanium dioxide, phenyl trimethicone, dioctyl adipate, and hexamethyl disiloxane.

Fragrance is also a desirable additional component. Suitable materials include conventional perfumes, such as perfume oils and also include so-called deo-perfumes, as described in EP 545,556 and other publications. Levels of incorporation are preferably up to 4% by weight, particularly from 0.1% to 2% by weight, and especially from 0.7% to 1.7% by weight.

EXAMPLES

The invention will now be illustrated further by the following non-limiting examples.

The raw materials indicated in Table 1 were used in the preparation of the Examples indicated below.

TABLE 1

| Name used | Chemical name or Trade name | INCI name | Supplier |
|---|---|---|---|
| Fatty acids | | | |
| Oleic acid | Oleic acid | Oleic Acid | TCI |
| Linoleic acid | Linoleic acid | Linoleic Acid | TCI |
| Linolenic acid | Linolenic acid | Linolenic Acid | TCI |
| Ricinoleic acid | Ricinoleic acid | Ricinoleic Acid | TCI |
| Emulsifiers | | | |
| Steareth-20 | Brij S20 | Steareth-20 | Croda |
| CAPB | Tegobetain F 50 | Cocamidopropyl betaine | Local producer |
| Brij S2 | Steareth-2 | Steareth-2 | Croda |
| SLES-3EO | Texapon N703GT [70% aqu. soln.] | Sodium laureth sulfate | BASF |
| Span 20 | Sorbitan monolaurate | Sorbitan Laurate | Croda |
| Tween 80 | Polyoxyethylene sorbitan monooleate | Polysorbate 80 | TCI |
| Triton X-100 | 4-(1,1,3,3-tetramethylbutyl)-phenyl-polyethylene glycol | Octoxynol-9 | Merck |
| LDAO | N,N-dimethyl-dodecylamine N-oxide (30% aqu. soln). | Lauryldimethylamine N-oxide | Sigma Aldrich |
| SME-C16 | Sulphonated methyl ester | Sodium methyl 2-sulfopalmitate | KLK Oleo |

TABLE 1-continued

| Name used | Chemical name or Trade name | INCI name | Supplier |
|---|---|---|---|
| Metal salts | | | |
| Calcium chloride | Calcium chloride dihydrate | Calcium chloride | Chem-Lab |
| Zinc chloride | Zinc chloride | Zinc Chloride | Sigma Aldrich |
| Thickeners | | | |
| Jaguar S | Guar gum | Cyamopsis tetragonoloba gum | Solvay Novecare |
| PEG 35000 | Poly(ethylene glycol) | — | Merck |
| Natrosol 250 HR | Hydroxyethylcellulose | Hydroxyethylcellulose | Ashland |
| Jaguar C-162 | Jaguar C-162 | Hydroxypropyl guar hydroxypropyl trimonium chloride | Solvay |
| SP-100 | N-Hance ™ SP-100 | Acrylamidopropyl trimonium chloride/ acrylamide copolymer | Ashland |
| Guar BF-7 | Esaflor BF 7 | Guar hydroxypropyltrimonium chloride | Lamberti |
| Silica particles | Hydrophobic pyrogenic silica (fumed silica) | — | Unilever |
| Preservatives | | | |
| 2-phenoxyethanol | 2-phenoxyethanol | Phenoxyethanol | Sigma-Aldrich |
| Glycacil L | Glycacil L | Iodopropynyl butylcarbamate PEG-4 laurate PEG-4 dilaurate Propylene glycol | Lonza |
| Polyglycerol emulsifiers | | | |
| PG-3-S | Polyaldo ® 3-1-S | Polyglyceryl-3 stearate | Lonza |
| PG-6-D | Polyaldo ® 6-2-S | Polyglyceryl-6 distearate | Lonza |
| PG-10-S | Polyaldo ® 10-1-S (pastillated) | Polyglyceryl-10 stearate | Lonza |
| PG-10-O | Polyaldo ® 10-1-O | Polyglyceryl-10 oleate | Lonza |
| PG-10-CC | Polyaldo ® 10-1-CC | Polyglyceryl-10 caprylate/caprate | Lonza |

Study 1

A simple emulsion composition comprising 7% oleic acid, 1.85% calcium chloride (always dihydrate in these Examples) and 1.6% Steareth-20 was prepared and adjusted to pH 3.5 with a small amount of hydrochloric acid. The emulsion was prepared at ambient temperature using a high shear mixer operating at 3500 rpm for 3 minutes and then at 24,000 rpm for 10 minutes. The emulsion had a milky white appearance and was stable for one month at ambient temperature.

Figure 2:
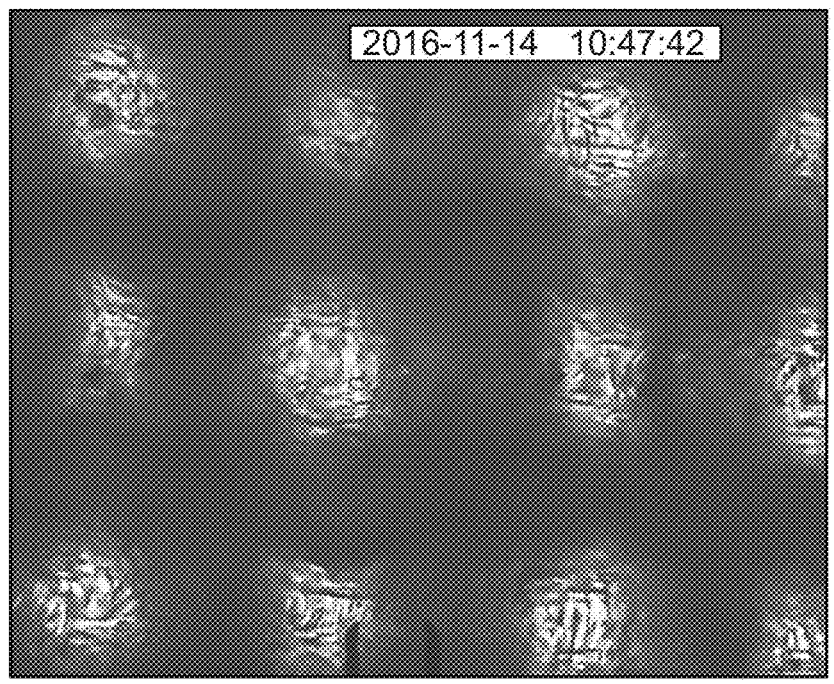
FIG. 2 is a microscopy image of treated cotton following adjustment of the composition on the cotton to pH 6.

2 ml of the emulsion composition was applied to a piece of woven cotton on a microscope slide. The woven cotton had a "pore size" (spaces between the warp and weft) of approximately 80 microns, which is comparable to the average pore size of sweat glands in the axillae (ca. 90 to 100 microns). FIG. 1 is a microscopy image of the treated fabric. The solid black lines on the lower edge are a scale bar representing 100 microns. Next, the pH of the composition on the cotton was adjusted to 6 using 6M sodium hydroxide solution (approximately 10 microlitres). Following the pH adjustment, the pores in the cotton fabric became blocked by a crystalline phase which glowed under the transmitted polarised light used for the study. FIG. 2 is a microscopy image of the treated cotton following adjustment to pH 6 (same magnification as FIG. 1).

This study illustrates the potential that compositions of the invention have for blocking pores having a diameter of about 80 microns, which include sweat pores in the underarm regions (axillae). The pH of the sweat on the skin in the axillae is typically about 6.5, so a composition prepared at pH 3.5 will increase in pH on topical application to the axillae by equilibration with its surroundings. As the pH increases, compositions of the invention cause in situ generation of a metal soap of the fatty acid which form "plugs" in the sweat glands and thereby reducing perspiration.

Study 2

In Study 1, the sample prepared was of low viscosity (5 mPa·s, measured as described below). In attempts to make more viscous samples (more suitable for use from roll-on dispensers), variants on the Study 1 composition were prepared using a variety of thickeners and emulsifiers. The samples were prepared as follows.

The thickener and/or emulsifier were dissolved in water with stirring. The pH of the resulting solution was adjusted to 3.5 with a small amount of hydrochloric acid. This solution was then poured over the fatty acid and the metal salt and preservative were added. The resulting emulsion premix was then sheared at 3500 rpm for 2 minutes and then at 15,000 rpm for 8 minutes. The components and amounts used are indicated in the relevant tables.

Examples 1 to 9

The Examples illustrated in Table 2 et seq were prepared as described above. As well as the compositional details, Table 2 details the viscosity of the composition as manufactured (at pH 3.5) and the viscosity of the composition following adjustment to pH 6 (with 6 M sodium hydroxide solution). The table also includes storage stability details for the compositions.

Throughout these examples:
Instability was manifested by phase separation.
Viscosities are only reported for samples that were stable for at least 1 week.
Viscosities are expressed in Pa·s and were measured at 37° C. Viscosities were measured over a range of shear rates, but those quoted are for the initial measurement at $0.01\ s^{-1}$. A Bohlin Gemini rheometer with cone and plate geometry was used.

The viscosity at pH at 3.5 is illustrative of the effectiveness of the thickening agent used.

The increase in viscosity on going from pH 3.5 to pH 6 is illustrative of the extent of gelation of the composition across this pH range and its potential for in situ sweat gland blockage on application to the axillae.

TABLE 2

| Component | Example |||||||||
| --- | --- | --- | --- | --- | --- | --- | --- | --- | --- |
|  | 1 | 2 | 3 | 4 | 5 | 6 | 7 | 8 | 9 |
| Oleic acid | 7 | 10.5 | 10.5 | 7 | 7 | 7 | 7 | 7 | 7 |
| Steareth-20 | 1.6 | 2.4 | 2.4 | 1.6 | 1.6 | 0.8 | 0.8 | 3.2 | 1.6 |
| CAPB | — | — | — | — | — | 0.8 | — | — | — |
| Steareth-2 | — | — | — | — | — | — | 0.8 | — | — |
| Calcium chloride | 1.85 | 2.775 | 2.775 | 1.85 | 1.85 | 1.85 | 1.85 | 1.85 | 1.85 |
| Jaguar S | 0.6 | 0.6 | — | — | — | 0.6 | 0.6 | 0.6 | — |
| Natrosol 250 HR | — | — | 0.65 | — | — | — | — | — | — |
| Jaguar C-162 | — | — | — | 0.8 | — | — | — | — | — |
| Guar BF-7 | — | — | — | — | 1.0 | — | — | — | — |
| SP-100 | — | — | — | — | — | — | — | — | 0.8 |
| Phenoxyethanol | 0.5 | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 | 0.05 |
| Water | To 100 |||||||||
| Viscosity at pH 3.5 | 1.5 | 1.8 | 4 | 4 | 4 | 3.5 | — | — | — |
| Viscosity at pH 6 | 18 | 3.5 | 275 | 5.5 | 5.5 | 5 | — | — | — |
| Stability at 25° C. (weeks) | 3 | 1 | 1 | 1 | 2 | 2 | 0 | 0 | 0 |

The molar ratio of oleic acid to calcium chloride in these examples was 2:1.

In Example 8, the ratio of emulsifier to fatty acid was 31.4:68.6. This sample was less stable than Example 1, which had a ratio of emulsifier to fatty acid of 16.7:83.3.

Examples 10 to 19

The Examples illustrated in Table 3 were prepared in the same manner as those in Table 2. Viscosities and stabilities were measured and assessed as described for the earlier examples.

TABLE 3

| Component | Example ||||||||||
| --- | --- | --- | --- | --- | --- | --- | --- | --- | --- | --- |
|  | 10 | 11 | 12 | 13 | 14 | 15 | 16 | 17 | 18 | 19 |
| Oleic acid | 7 | 7 | 7 | 7 | 7 | 7 | 7 | 7 | 7 | 7 |
| Steareth-20 | 0.8 | 0.8 | 1.6 | 0.8 | 1.4 | 1 | 1.6 | 0.8 | 0.8 | 0.8 |
| SLES-3EO | 0.8 | — | — | 0.8 | 0.2 | 0.6 | — | 0.8 | 0.8 | 0.8 |
| Steareth-2 | — | — | 0.3 | — | — | — | — | — | — | — |
| Span 20 | — | 0.4 | — | — | — | — | — | — | — | — |
| Tween 80 | — | 0.4 | — | — | — | — | — | — | — | — |
| Calcium chloride | 1.85 | 1.85 | 1.85 | 2.4 | 1.85 | 1.85 | 1.85 | 1.85 | 1.85 | 2.6 |
| Jaguar S | 0.6 | 0.6 | 0.6 | 0.55 | 0.6 | 0.6 | — | 0.5 | 0.58 | 0.55 |
| Silica particles | — | — | — | — | — | — | 0.7-2.0 | — | — | — |
| Phenoxyethanol | 0.5 | 0.5 | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 | 0.05 | 0.05 |
| Water | To 100 ||||||||||
| Viscosity at pH 3.5 | 3 | — | — | 3.65 | 2.6 | 3.3 | — | 1.4 | 3.5 | 1.3 |
| Viscosity at pH 6 | 10.5 | — | — | 5.3 | 4.2 | 5.6 | — | 3.5 | 9 | 2.3 |
| Stability at 25° C. (weeks) | 8 | 0 | 0 | 2 | 1 | 1 | 0 | 5 | 5 | 5 |

Example 16 comprised 4 samples with different levels of silica: 0.7, 1, 1.4 and 2% by weight. None of these samples proved stable for one week. Examples 11 and 12 also proved to be have similar instability.

Viscosities were measured for the samples having at least one week's stability. The most promising sample from this set was Example 10, which was stable for 8 weeks and increased in viscosity from 3 Pa·s to 10.5 Pa·s on going from pH 3.5 to pH 6.

Examples 20 to 26

The Examples illustrated in Table 4 were prepared in the same manner as those in Table 2. Viscosities and stabilities were measured and assessed as described for the earlier examples. In addition, a further study ("Study 3", details below) was made on these Examples.

TABLE 4

| Component | Example | | | | | | |
|---|---|---|---|---|---|---|---|
| | 20 | 21 | 22 | 23 | 24 | 25 | 26 |
| Oleic acid | — | — | — | — | — | — | 3.5 |
| Linoleic acid | 7 | — | 7 | — | 3.5 | 3.5 | — |
| Linolenic acid | — | 7 | — | 7 | 3.5 | 3.5 | 3.5 |
| Steareth-20 | 1.6 | 1.6 | 0.8 | 0.8 | 1.6 | 0.8 | 0.8 |
| SLES-3EO | — | — | 0.8 | 0.8 | — | 0.8 | 0.8 |
| Calcium chloride | 1.85 | 1.85 | 1.85 | 1.85 | 1.85 | 1.85 | 1.85 |
| Jaguar S | 0.6 | 0.6 | 0.6 | 0.6 | 0.6 | 0.6 | 0.6 |
| Phenoxyethanol | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 |
| Water | | | | To 100 | | | |
| Viscosity at pH 3.5 | 2 | 2.3 | 1.5 | 1.3 | 2 | 3.5 | 3.3 |
| Viscosity at pH 6 | 4 | 3.7 | 7.8 | 6 | 3.7 | 9 | 3.6 |
| Stability at 25° C. (weeks) | 3 | 3 | 3 | 3 | 1 | 1 | 1 |
| P value (Pa) | 1072 | 1224 | 935 | 2510 | 692 | 567 | 533 |

Study 3

Figure 3:
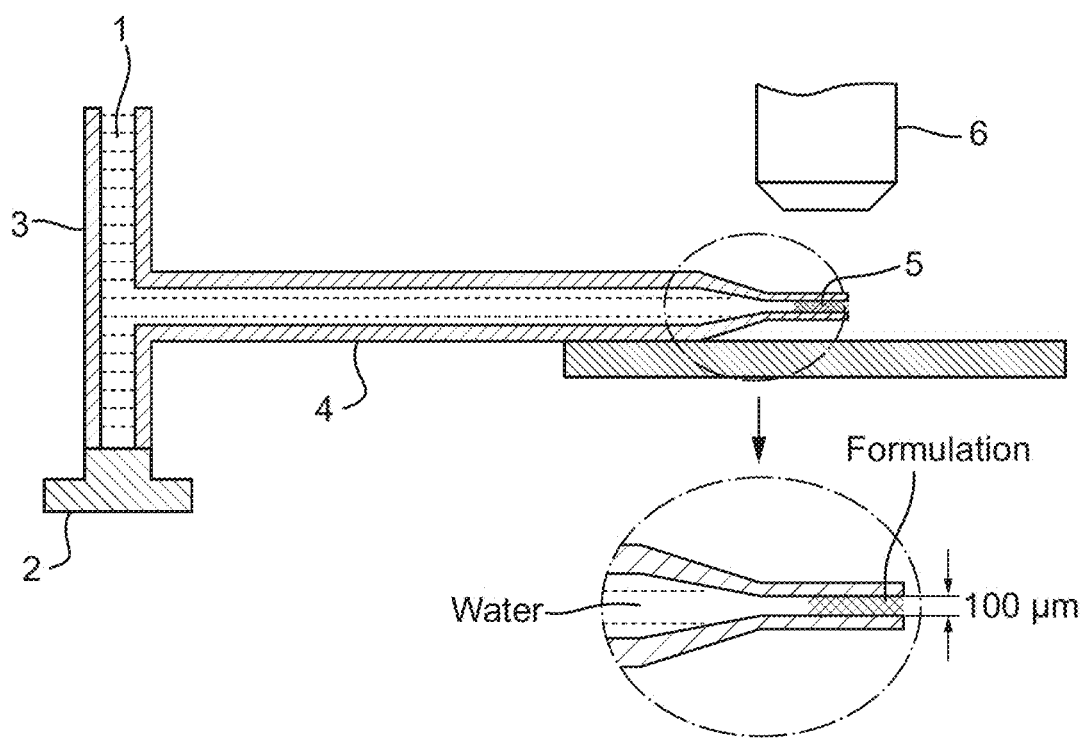
FIG. 3 illustrates a schematic representation of a "capillary unclogging" equipment for assessing the potential for sweat pore blockage of a composition.

This further study assessed the potential for sweat pore blockage by the compositions detailed in Table 4 (and others) using a "capillary unclogging" experiment. The equipment used is schematically represented in FIG. 3. The equipment comprised a pressure control (1) and a pressure transducer* (2) for pressuring a fluid within a tube (3) therebetween. Branching off orthogonally from the tube (3) is a capillary (4) which narrows to a terminal section (5) having a diameter of 100 microns. It will be noted that this dimension is similar to that of diameter of sweat pores in the of human body (vide supra).

A piezoelectric crystal, PX26-005GV (range 0-5 PSIG) from OMEGA.

Directly above the terminal section (5) sits the objective (6) of a microscope (not illustrated) working in reflected light.

In a first step, the capillary (4) is filled with artificial sweat, the composition of which is indicated below in Table 5. This is done using the pressure control (1), the location of which is illustrated in FIG. 3. In this step, the pressure controller (1) is used to draw the artificial sweat into the capillary (4) through the terminal section (5).

In a second step, approximately 10 μl of the composition to be assessed is drawn into the terminal section (5) of the capillary (4), again by use of pressure controller (1).

In a third step, the system is allowed to equilibrate for 15 minutes. Throughout this period, and throughout the entire process, the temperature is maintained at 25° C. This equilibration period allows for the potential interaction of the composition with the artificial sweat and potential gelation and blockage of the terminal section (5) of the capillary (4).

In a fourth step, the pressure control (1) is used to make small step changes (increases) in the internal pressure. Between each step change in pressure, a pause is taken to allow constant pressure to be re-established. During this process, the presence or otherwise of any gel plug in the terminal section (5) of the capillary (4) is monitored using the microscope. Pressure is increased in this manner until any gel plug is pushed out of terminal section (5) of the capillary (4). The pressure (P) required to eject the gel plug is a measure of the strength of the gel formed between the artificial sweat and the composition being tested. This in turn, is an indication of the effectiveness of the composition as an antiperspirant.

TABLE 5

Artificial Sweat Composition

| Component | Amount (%) |
|---|---|
| Lactic acid | 0.0901 |
| Potassium chloride | 0.0373 |
| Sodium chloride | 0.2098 |
| Ammonium chloride | 0.0107 |
| Calcium chloride | 0.0222 |
| Urea | 0.0018 |
| Sodium bicarbonate* | 0.2025 |
| Water | To 100 |

*The sodium bicarbonate is added immediately before use and results in a pH of 6.9.

The results given at the bottom of Table 4 indicate that each of the compositions produced a gel plug on contact with the artificial sweat and that some compositions gave gel plugs requiring greater than 1 MPa force to eject them from the terminal section (5) of the capillary (6).

Some of the examples described earlier were also evaluated using the capillary unclogging method of Study 3. The results are presented in Table 6.

TABLE 6

| Example | P value (Pa) |
|---|---|
| 1 | 304 |
| 10 | 1046 |
| 17 | 690 |

TABLE 6-continued

| Example | P value (Pa) |
|---|---|
| 18 | 843 |
| 19 | 860 |

The Examples illustrated in Table 7 were prepared in the same manner as those in Table 2. Viscosities and stabilities were measured and assessed as described for the earlier examples.

TABLE 7

| Component | 27 | 28 | 29 | 30 | 31 | 32 | 33 | 34* | 35* |
|---|---|---|---|---|---|---|---|---|---|
| Oleic acid | — | — | — | — | — | — | 7 | 7 | — |
| Linoleic acid | — | 7 | — | — | — | — | — | — | — |
| Linolenic acid | 7 | — | 7 | 7 | 7 | 7 | — | — | 7 |
| Steareth-20 | — | — | 0.8 | 0.8 | — | — | — | 0.8 | 0.8 |
| SLES-3EO | — | 0.8 | 0.8 | 0.8 | 1.3 | — | — | 0.8 | 0.8 |
| Triton X-100 | 1.6 | 0.8 | — | — | — | — | — | — | — |
| LDAO | — | — | — | — | 0.3 | 0.3 | 0.3 | — | — |
| SME-C16 | — | — | — | — | — | 1.3 | 1.3 | — | — |
| Calcium chloride | 1.85 | 1.85 | 1.85 | 1.85 | 1.85 | 1.85 | 1.85 | 1.85 | 1.85 |
| Zinc chloride | — | — | — | — | — | — | — | — | — |
| Jaguar S | 0.6 | 0.6 | 0.3 | — | 0.6 | 0.6 | 0.6 | 0.6 | 0.6 |
| PEG 35000 | — | — | 0.3 | 1 | — | — | — | — | — |
| Phenoxyethanol | 0.5 | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 | 0.05 |
| Water | | | | | To 100 | | | | |
| Viscosity at pH 3.5 | — | — | — | — | — | — | — | 3.5 | 2.6 |
| Viscosity at pH 6 | — | — | — | — | — | — | — | 6.8 | 6.2 |
| Stability at 25° C. (weeks) | 0 | 0 | 0 | 0 | 0 | 0 | 0 | 1 | 1 |

*In addition to the processing conditions indicated for the previous Examples, these Examples were prepared using Ultrasound stirring.

Examples 27 to 33 illustrate that whilst samples can be prepared with a range of emulsifiers, they can be difficult to stabilize. Earlier examples (e.g. Example 1, Example 10 and Examples 20-23) have illustrated that reasonably stable emulsions can be formed with Jaguar S thickener and simple nonionic emulsifiers like Steareth-20 or with blends of nonionic emulsifier and anionic emulsifier, like Steareth-20 and SLES-3EO. By contrast, Example 31 to 33 illustrate that blends of zwitterionic emulsifier (LDAO) and anionic emulsifier (SLES-3EO or SME-C16) are less successful.

Of the examples illustrated in Table 7, only Examples 34 and 35 were stable for 1 week.

The Examples illustrated in Table 8 were prepared in the same manner as those in Table 2. Viscosities and stabilities were measured and assessed as described for the earlier examples and P values were assessed in accordance with the protocol of Study 3.

TABLE 8

| Component | 36 | 37 | 38 | 39 | 40 | 41 | 42 | 43 | 44 |
|---|---|---|---|---|---|---|---|---|---|
| Oleic acid | — | — | — | 7 | 7 | — | — | 7 | — |
| Linolenic acid | — | — | 7 | — | — | 7 | — | — | 7 |
| Ricinoleic acid | 7.6 | 7.6 | — | — | — | — | 7.6 | — | — |
| Steareth-20 | 0.8 | 0.8 | 0.8 | 0.8 | 0.8 | 0.8 | 1.6 | 1.6 | 1.6 |
| SLES-3EO | 0.8 | 0.8 | 0.8 | 0.8 | 0.8 | 0.8 | — | — | — |
| Zinc chloride | 1.7 | — | — | — | 1.7 | 1.7 | 1.7 | 1.7 | 1.7 |
| Jaguar S | 0.6 | 0.6 | 0.6 | 0.6 | 0.6 | 0.6 | 0.6 | 0.6 | 0.6 |
| Phenoxyethanol | 0.5 | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 | 0.05 |
| Water | | | | | To 100 | | | | |
| Viscosity at pH 3.5 | 3 | 3 | 2 | 2.4 | 3.8 | 3.5 | 4 | 3.2 | 4 |
| Viscosity at pH 6 | 13 | 10.7 | 15.7 | 7.3 | 10 | 9 | 225 | 11 | 9 |

TABLE 8-continued

| | Example | | | | | | | | |
|---|---|---|---|---|---|---|---|---|---|
| Component | 36 | 37 | 38 | 39 | 40 | 41 | 42 | 43 | 44 |
| Stability at 25° C. (weeks) | 3 | 1 | 1 | 1 | 3 | 3 | 3 | 2 | 1 |
| P value (Pa) | 850 | 985 | 805 | 780 | 601 | 750 | 1150 | 960 | 1025 |

Example 42 demonstrated a remarkable high increase in viscosity on changing the pH from 3.5 to 6. This example was subjected to an in vivo antiperspirancy assessment in "Study 4" (vide infra).

The Examples illustrated in Table 9 were prepared in the same manner as those in Table 2. Viscosities and stabilities were measured and assessed as described for the earlier examples and P values were assessed in accordance with the protocol of Study 3.

The molar ratio of fatty acid to calcium chloride in these examples was 1:1 or less.

TABLE 9

| | Example | | | | | |
|---|---|---|---|---|---|---|
| Component | 45 | 46 | 47 | 48 | 49 | 50 |
| Oleic acid | 3.5 | 3.5 | — | — | — | 3.5 |
| Linoleic acid | — | — | 3.5 | — | — | — |
| Linolenic acid | — | — | — | 3.5 | — | — |
| Ricinoleic acid | — | — | — | — | 3.5 | — |
| Steareth-20 | 1.6 | 0.8 | 0.8 | 0.8 | 1.6 | 1.6 |
| SLES-3EO | — | 0.8 | 0.8 | 0.8 | — | — |
| Calcium chloride | 1.85 | 1.85 | 1.85 | 1.85 | — | — |
| Zinc chloride | — | — | — | — | 1.7 | 1.7 |
| Jaguar S | 0.6 | 0.6 | 0.6 | 0.6 | 0.6 | 0.6 |
| PEG 35000 | — | — | — | — | — | — |
| Phenoxyethanol | 0.5 | 0.5 | 0.5 | 0.5 | 0.5 | 0.5 |
| Glycacil L | 0.05 | 0.05 | 0.05 | 0.05 | 0.05 | 0.05 |
| Water | To 100 | | | | | |
| Viscosity at pH 3.5 | 1.4 | 0.5 | 1 | 0.5 | 3.8 | 1.2 |
| Viscosity at pH 6 | 2.2 | 1.1 | 16.8 | 7.9 | 45 | 425 |
| Stability at 25° C. (weeks) | 3 | 3 | 3 | 3 | 3 | 3 |
| P value (Pa) | 550 | 1070 | 601 | 642 | 625 | 615 |

The Examples illustrated in Tables 10 to 12 were prepared in the manner described below.

Viscosities and stabilities were measured and assessed as described for the earlier examples.

To prepare the samples, the emulsifier(s) was/were dissolved in water with stirring and heating to 70° C. The resulting solution was allowed to return to room temperature and thickener was then added with use of a Silverson L4RT homogeniser, operating for 10 mins at 5000 rpm. The fatty acid was then added dropwise, using the homogeniser for 10 mins at 7500 rpm. The water-soluble metal salt was then added, using the homogeniser for 3 mins at 7500 rpm. Finally, the preservatives were added, using the homogeniser for 2 mins at 7500 rpm. The components and amounts used are indicated in the tables.

TABLE 10

| Component | Example | | | | | | | |
|---|---|---|---|---|---|---|---|---|
| | 51 | 52 | 53 | 54 | 55 | 56 | 57 | 58 |
| Oleic acid | 7 | 7 | 7 | 7 | 7 | 7 | 7 | 7 |
| Steareth-20 | — | — | — | 0.8 | — | 0.8 | 0.8 | — |
| PG-3-S | — | — | — | 1 | 2 | 2 | — | 1 |
| PG-6-DS | 1 | — | — | — | — | — | 1 | 1 |
| PG-10-S | — | 1 | 1 | — | — | — | — | — |
| PG-10-O | — | — | 1 | — | — | — | — | — |
| PG-10-CC | 1 | 1 | — | — | — | — | — | — |
| Calcium chloride | 1.85 | 1.85 | 1.85 | 1.85 | 1.85 | 1.85 | 1.85 | 1.85 |
| Jaguar S | 0.6 | 0.6 | 0.6 | 0.6 | 0.6 | 0.6 | 0.6 | 0.6 |
| Phenoxyethanol | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 |
| Water | To 100 | | | | | | | |
| Viscosity (pH 3.5) | 3 | 2.7 | 3.2 | 3.2 | 0.6 | 0.8 | 3.5 | 4.8 |
| Viscosity (pH 6) | 2.8 | 3 | 3.3 | 7 | 8.8 | 2.4 | 4.9 | 9.3 |
| Stability at 25° C. (weeks) | 2 | 2 | 2 | 2 | 2 | 2 | 2 | 2 |

The examples in Table 10 each comprised a polyglyceryl emulsifier and each had a stability of 2 weeks at 25° C. In addition, each demonstrated an increase in viscosity on changing the pH from 3.5 to 6.

The examples in Table 11 also comprised a polyglyceryl emulsifier and each had reasonable stability at 25° C. In addition, each demonstrated an increase in viscosity on changing the pH from 3.5 to 6. Example 59 exhibited a particularly high increase in viscosity on changing the pH from 3.5 to 6.

TABLE 11

| Component | Example | | | | | | | |
|---|---|---|---|---|---|---|---|---|
| | 59 | 60 | 61 | 62 | 63 | 64 | 65 | 66 |
| Oleic acid | 7 | 7 | 7 | 7 | — | — | — | — |
| Ricinoleic acid | — | — | — | — | 7.6 | 7.6 | 7.6 | 7.6 |
| Steareth-20 | — | — | — | 0.8 | — | 0.8 | — | — |
| PG-3-S | 2 | — | — | 1 | — | 1 | — | — |
| PG-6-DS | 2 | 1 | — | — | — | — | 1 | — |
| PG-10-S | — | — | 1 | — | 1 | — | — | 1 |
| PG-10-O | — | — | — | — | — | — | — | 1 |
| PG-10-CC | — | 1 | 1 | — | 1 | — | 1 | — |
| Zinc chloride | 1.7 | 1.7 | 1.7 | 1.7 | 1.7 | 1.7 | 1.7 | 1.7 |
| Jaguar S | 0.6 | 0.6 | 0.6 | 0.6 | 0.6 | 0.6 | 0.6 | 0.6 |
| Phenoxyethanol | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 |
| Water | To 100 | | | | | | | |
| Viscosity (pH 3.5) | 5 | 4 | 3.5 | 3.1 | 2.2 | 3.6 | 2.6 | 3.9 |
| Viscosity (pH 6) | 115 | 26 | 36 | 17 | 9 | 11.6 | 18 | 31 |
| Stability at 25° C. (weeks) | 4 | 2 | 2 | 1 | 2 | 2 | 1 | 2 |

The examples in Table 12 also comprised a polyglyceryl emulsifier and each had reasonable to good stability at 25° C. Examples 68 and 70 demonstrated particularly good stability.

Many examples in Table 12 also demonstrated a particularly high increase in viscosity on changing the pH from 3.5 to 6. Examples 67 to 70 and 73 to 74 were notable in this regard.

TABLE 12

| Component | 67 | 68 | 69 | 70 | 71 | 72 | 73 | 74 | 75 | 76 |
|---|---|---|---|---|---|---|---|---|---|---|
| Oleic acid | 7 | — | 7 | 7 | 7 | 7 | 7 | 7 | — | 7 |
| Ricinoleic acid | — | 7.6 | — | — | — | — | — | — | 7.6 | — |
| PG-3-S | — | 1 | 1 | 2 | 1 | 3 | 1 | 3 | 1 | 2 |
| PG-6-DS | — | 1 | 1 | 2 | 3 | 1 | 3 | 1 | 1 | 2 |
| PG-10-S | 1 | — | — | — | — | — | — | — | — | — |
| PG-10-O | 1 | — | — | — | — | — | — | — | — | — |
| PG-10-CC | 1 | — | — | — | — | — | — | — | — | — |
| Calcium chloride | — | — | — | — | 1.85 | 1.85 | — | — | — | — |
| Zinc chloride | 1.7 | 1.7 | 1.7 | 1.7 | — | — | 1.7 | 1.7 | 1.7 | 1.7 |
| Jaguar S | 0.6 | 0.6 | 0.6 | 0.6 | 0.6 | 0.6 | 0.6 | 0.6 | — | — |
| Phenoxyethanol | 0.5 | 0.5 | 0.5 | 0.5 | 0.5 | 0.5 | 0.5 | 0.5 | 0.5 | 0.5 |
| Glycacil L | 0.05 | 0.05 | 0.05 | 0.05 | 0.05 | 0.05 | 0.05 | 0.05 | 0.05 | 0.05 |
| Water | | | | | To 100 | | | | | |
| Viscosity (pH 3.5) | 1.6 | 74 | 4.3 | 15 | 17 | 7.6 | 15 | 6.6 | — | — |
| Viscosity (pH 6) | 120 | 223 | 274 | 393 | 57 | 10 | 211 | 283 | — | — |
| Stability at 25° C. (weeks) | 3 | 6 | 3 | 5 | 3 | 3 | 3 | 2 | 1 | 1 |

Study 4

An example essentially the same* as Example 1 and Example 42 were assessed in vivo for antiperspirancy performance.

Prepared in same manner, but comprising 8% oleic acid and 1% less water. Referred to herein as Example 1A.

The method used was a sauna back protocol (as published by Brandt, Bielfeldt, Springmann & Wilhelm, *Influence of climatic conditions on antiperspirant efficacy determined at different test areas*, Skin Research and Technology, 2018, 14:213-219) and is a well-established in vivo screen for antiperspirant efficacy. In such studies, regular sauna users have 16 test sites marked on the back to compare 8 products with 8 control sites contralaterally. Product application is repeated for 4 consecutive days, with a gravimetric assessment of sauna induced sweating carried out on day 5.

Sixteen test areas (size: 4 cm by 5 cm) are marked using a waterproof pen (8 test sites on each side of the spine). The two test fields located contra-lateral on the right and the left side of the spine are considered as a pair and are used for comparison of a test product and an untreated control area. The treated and untreated side of the back alternate between subjects. Furthermore, test areas are assigned by cyclic permutation.

On days 1 to 4, each of 8 test products is applied and evenly distributed on its test area (dosage: 75 µl). After application, the subjects rest for approximately 5 minutes to allow the test products to absorb into the skin. Afterwards, all test and control areas are covered with occlusive non-absorbent patches. Subjects then leave the test centre and returned 2 hours (±5 min) later when the patches are removed.

On day 5, the back of the subjects is cleaned with water and dried with a paper towel. All test areas, as well as untreated contralateral areas, are covered with pre-weighed absorbent pads on plastic sheets (attached to the back with Fixomull®). The subjects then lay in prone position in a sauna at approximately 80° C. for about 15 minutes. Directly after leaving the sauna, all pads are removed with tweezers and put into cups. Gravimetrical measurements of pads are performed immediately.

The above method was used to independently test the in vivo antiperspirancy performance of Example 1A and Example 42.

In the evaluation of Example 1A, 25 female panelists were employed and all 25 completed the test. Example 1A was found to give a Sweat Weight Reduction (SWR) of 9% greater than the untreated control site, significant at the 95% level.

In the evaluation of Example 42, 25 female panelists were employed, 24 of whom completed the test. Example 42 was found to give an SWR of 29% greater than the untreated control site, significant at the 99% level.

The invention claimed is:

1. An oil-in-water emulsion comprising:
   (i) a $C_{10}$-$C_{22}$ fatty acid that is a liquid at one atmosphere pressure and 25° C.;
   (ii) an emulsifier for the $C_{10}$-$C_{22}$ fatty acid; and
   (iii) a water-soluble metal salt that forms a water-insoluble salt with the $C_{10}$-$C_{22}$ fatty acid at a pH of greater than 6;
   wherein the oil-in-water emulsion does not comprise aluminum salts or zirconium salts;
   wherein the water-soluble metal salt is divalent;
   wherein a molar ratio of the $C_{10}$-$C_{22}$ fatty acid to a cation of the water-soluble metal salt divided by a cation of the water-soluble metal salt's valence is from 1:2 to 2:1;
   and further wherein the oil-in-water emulsion increases by at least 1 pH unit after application to a skin surface, which results in gelation of the oil-in-water emulsion comprising the water-soluble metal salt and the $C_{10}$-$C_{22}$ fatty acid.

2. The oil-in-water emulsion according to claim 1, wherein the $C_{10}$-$C_{22}$ fatty acid is unsaturated.

3. The oil-in-water emulsion according to claim 2, wherein the $C_{10}$-$C_{22}$ fatty acid is selected from the group consisting of oleic acid, linoleic acid, linolenic acid, ricinoleic acid, and a combination thereof.

4. The oil-in-water emulsion according to claim 3, wherein the $C_{10}$-$C_{22}$ fatty acid is selected from the group consisting of oleic acid, ricinoleic acid, and a combination thereof.

5. The oil-in-water emulsion according to claim 1, wherein the water-soluble metal salt is selected from a group consisting of a calcium salt, a zinc salt, and a combination thereof.

6. The oil-in-water emulsion according to claim 5, wherein the water-soluble metal salt is a calcium salt.

7. The oil-in-water emulsion according to claim 1, further comprising a thickening agent.

8. The oil-in-water emulsion according to claim 7, wherein the thickening agent is a cationic polymer or nonionic polymer.

9. The oil-in-water emulsion according to claim 8, wherein the thickening agent is selected from the group consisting of guar gum, guar gum derivatives, cellulose derivatives, and a combination thereof.

10. A method of reducing perspiration comprising a step of topically applying to a skin the oil-in-water emulsion according to claim 1.

11. The oil-in-water emulsion according to claim 5, wherein the water-soluble metal salt is selected from the group consisting of calcium chloride, zinc chloride, and a combination thereof.

12. The oil-in-water emulsion according to claim 1, wherein the $C_{10}$-$C_{22}$ fatty acid comprises 18 carbon atoms.

13. The oil-in-water emulsion according to claim 1, wherein the oil-in-water emulsion comprises from 3 to 15% of $C_{10}$-$C_{22}$ fatty acid by weight of the oil-in-water emulsion.

14. The oil-in-water emulsion according to claim 1, wherein the oil-in-water emulsion comprises from 0.75 to 3% of water-soluble metal salt by weight of the oil-in-water emulsion.

15. The oil-in-water emulsion according to claim 1, wherein the oil-in-water emulsion increases by at least 1 pH unit after application to a skin surface having perspiration.

16. The oil-in-water emulsion according to claim 1, wherein the oil-in-water emulsion comprises from 0.5 to 10% of emulsifier by weight of the oil-in-water emulsion.

17. The oil-in-water emulsion according to claim 1, wherein a weight ratio of the emulsifier to $C_{10}$-$C_{22}$ fatty acid is from 1:10 to 2:3.

18. The oil-in-water emulsion according to claim 1, wherein the oil-in-water emulsion has a pH ranging from 3.5 to 4.5.

\* \* \* \* \*